Figure 1:
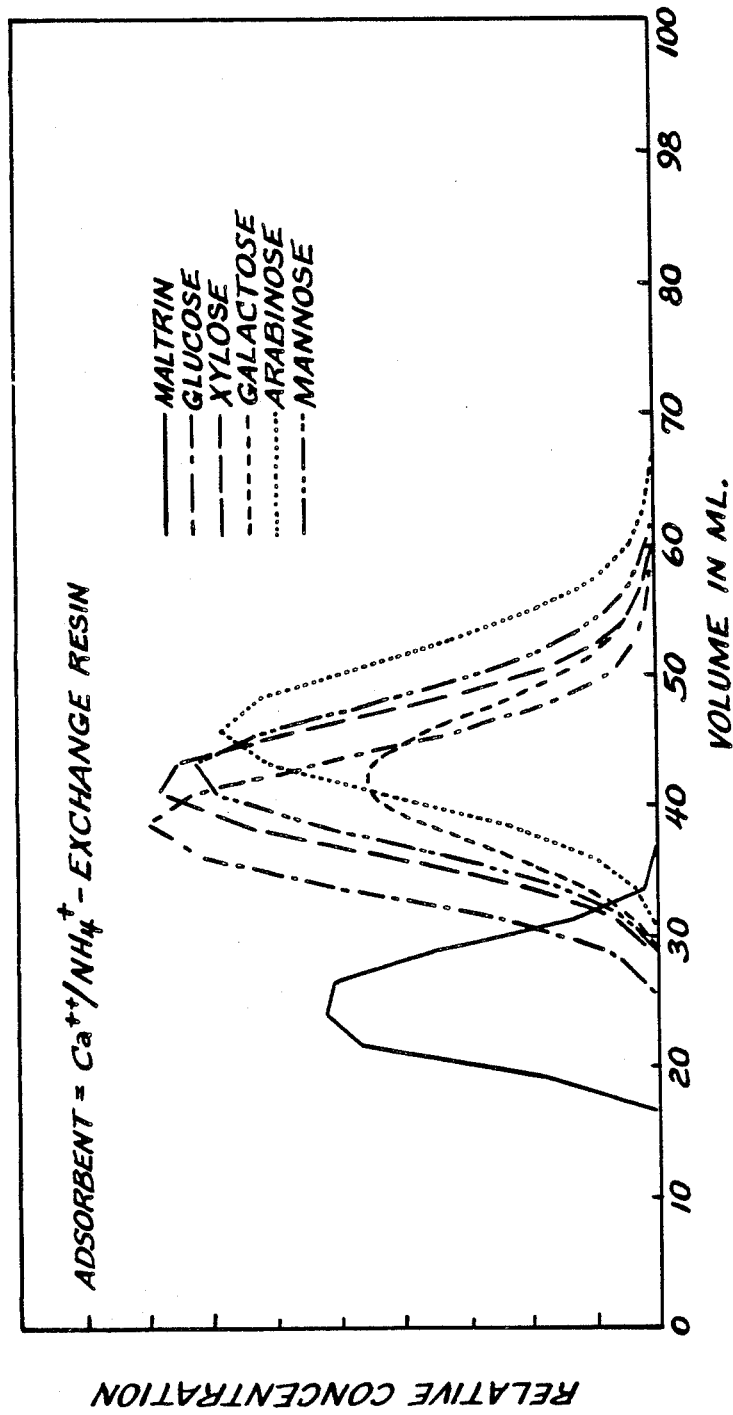

United States Patent [19]

Kulprathipanja

[11] Patent Number: 4,880,919
[45] Date of Patent: Nov. 14, 1989

[54] PROCESS FOR SEPARATING ARABINOSE FROM A MIXTURE OF ALDOSES

[75] Inventor: Santi Kulprathipanja, Des Plaines, Ill.

[73] Assignee: UOP, Des Plaines, Ill.

[21] Appl. No.: 948,384

[22] Filed: Dec. 31, 1986

[51] Int. Cl.$^4$ ............................ C07H 1/06; C13K 1/00
[52] U.S. Cl. ..................................... 536/127; 536/1.1; 536/124; 127/46.1; 127/46.3
[58] Field of Search ................... 536/124, 127, 1.1; 127/46.1, 46.3

[56] References Cited

U.S. PATENT DOCUMENTS

| | | | |
|---|---|---|---|
| 2,524,414 | 10/1950 | Wolfrom | 536/127 |
| 2,982,749 | 5/1961 | Friedrich et al. | 260/23 |
| 3,160,624 | 12/1964 | Iwai et al. | 260/209 |
| 4,226,977 | 10/1980 | Neuzil et al. | 536/127 |
| 4,238,243 | 12/1980 | Tu et al. | 536/127 |
| 4,287,001 | 9/1981 | Kulprathipanja et al. | 536/127 |
| 4,295,994 | 10/1981 | Kulprathipanja | 536/127 |
| 4,298,501 | 11/1981 | Kulprathipanja | 536/127 |
| 4,325,742 | 4/1982 | Arena | 536/1.1 |
| 4,337,171 | 6/1982 | Kulprathipanja et al. | 536/1.1 |
| 4,442,285 | 4/1984 | Neuzil et al. | 536/127 |
| 4,444,961 | 4/1984 | Timm | 526/88 |
| 4,471,114 | 9/1984 | Sherman et al. | 536/127 |
| 4,516,566 | 5/1985 | Chao et al. | 127/46.3 |

OTHER PUBLICATIONS

Spent Sulphite Liquor VII, "Sugar-Lignin Sulphonate Separations Using Ion Exchange Resins", Vincent F. Felicetta, Michael Lung, and Joseph L. McCarthy, vol. 42, No. 6, Jun. 1959, pp. 496-502.
Jandera et al., J. of Chromatography, 98, (1974), 55-104, p. 81.

Primary Examiner—Ronald W. Griffin
Assistant Examiner—Nancy S. Carson
Attorney, Agent, or Firm—Thomas K. McBride; John F. Spears, Jr.; Jack H. Hall

[57] ABSTRACT

Arabinose is separated from mixtures of monosaccharides containing arabinose and other aldopentoses and aldohexoses by adsorption on sulfonated polystyrene divinylbenzene crosslinked ion exchange resins exchanged with calcium-ammonium cationic and desorbing the adsorbate with water. The other saccharides are removed from the adsorption process in the raffinate.

7 Claims, 2 Drawing Sheets

PROCESS FOR SEPARATING ARABINOSE FROM A MIXTURE OF ALDOSES

BACKGROUND OF THE INVENTION

1. Field of the Invention

The field of art to which this invention pertains is the solid bed adsorptive separation of monosaccharides. More specifically, the invention relates to a process for separating arabinose from a mixture comprising arabinose and one or more additional aldoses, which process employs an adsorbent comprising a nuclearly sulfonated cation exchange resin having a crosslinked vinylaromatic resin matrix to selectively adsorb arabinose from the feed mixture.

2. Description of the Prior Art

This invention is particularly concerned with the separation of arabinose from other monosaccharides. Obtaining pure L-arabinose has commercial significance in light of its potential as a starting material for the production of L-glucose, a possible non-nutritive sweetener. Furthermore, L-arabinose is one of the few L-sugars available freely in nature, such as from sugar beet pulp and rice hulls, and therefore useful in synthesizing possibly non-nutritive sweeteners, such as L-glucose. Another common source of arabinose is the hydrolysis of hemicellulose in making pulp from wood which yields a mixture of L-arabinose, mannose and xylose. L-Arabinose, mixed with D-galactose and sucrose, are the products of a biomass operation to convert sugar beets to sugars. Regardless of the source, the arabinose is typically found in a mixture of many monosaccharides. Therefore, it is highly desirable to have a simple method for separating arabinose from the other monosaccharides present in the source mixture. However, in light of the ultimate food use of products made from arabinose, the separation process must not introduce contaminants that will render the arabinose or subsequent products unsuitable for human consumption.

Specific methods for separating arabinose are known in the art. U.S. Pat. No. 3,160,624 discloses the separation of D(L)-arabinose from D(L)-ribose by chromatography using a cellulose powder or ion exchanged resin. However, it is well known in the art that heretofore resin or cellulose adsorbents posed significant operational problems when their use is attempted on a large scale due to the high pressure drops associated with their use. However, newly developed methods of forming the ion exchange resins into very uniform spheres, as in U.S. Pat. No. 4,444,961 referred to hereinafter, reduce this tendency to cause high pressure drops. The zeolite adsorbents which are commonly used in large scale adsorptive separation processes have also been applied to the separation of arabinose from other mixtures of monosaccharides. U.S. Pat. No. 4,516,566 is directed to the separation of L-arabinose from a mixture of sugar that exists in the hydrolysates of wood and beet pulp using an X type zeolite exchanged with barium cations as an adsorbent. It is also disclosed in U.S. Pat. No. 4,471,114, at column 7, lines 31-44 that arabinose can be separated from mannose plus other sugars in two stages with a barium-exchanged X zeolite. A calcium-exchanged ion exchange resin (Dowex 50-W-X8) has been reported to separate arabinose from xylose and the carbonate form reported to separate arabinose from xylose, ribose and lyxose. P. Jandera et al., J. of Chromatography, 98 (1974) 55-104, p. 81.

In contradistinction to these findings, it has been discovered that nuclearly sulfonated cation exchange resins having a crosslinked vinylaromatic resin matrix will selectively adsorb arabinose from other monosaccharide aldoses. Moreover, the use of these ion exchange resins exchanged with a Ca—$NH_4$ mixture of cations allows the purification and recovery of arabinose that is acceptable to the food industry.

SUMMARY OF THE INVENTION

It is accordingly a broad objective of the present invention to provide a process for the separation of arabinose from a feed mixture containing arabinose and aldopentoses or aldohexoses using an ion exchange resin exchanged with calcium and ammonium cations at cation exchanged sites.

In brief summary, the present invention is a process for economically separating arabinose from a feed mixture comprising arabinose and at least one other monosaccharide selected from the group consisting of aldopentoses and aldohexoses. The process comprises contacting at adsorption conditions the monosaccharide mixture with an adsorbent comprising a cationic exchange resin containing a mixture of calcium and ammonium cations at the exchangeable cationic sites, selectively adsorbing arabinose to the substantial exclusion of the other monosaccharides, removing the nonadsorbed portion of the feed mixture from contact with the adsorbent, and thereafter recovering a purified arabinose by desorption at desorption conditions. Other objectives and embodiments of the present invention relate to specific feed mixtures, adsorbents, desorbent materials, operating conditions and flow configurations all of which are hereinafter disclosed in the following discussion of the present invention.

DESCRIPTION OF THE INVENTION

At the outset, the definitions of various terms used throughout the specification will be useful in making clear the operation, objects and advantages of this process.

A "feed mixture" is a mixture containing one or more extract components and one or more raffinate components to be separated by this process. The term "feed stream" indicates a stream of a feed mixture which passes to the adsorbent used in the process.

An "extract component" is a component that is more selectively adsorbed by the adsorbent while a "raffinate component" is a component that is less selectively adsorbed. The term "desorbent material" shall mean generally a material capable of desorbing an extract component. The term "desorbent stream" or "desorbent input stream" indicates the stream through which desorbent material passes to the adsorbent. The term "raffinate stream" or "raffinate output stream" means a stream through which a raffinate component is removed from the adsorbent. The composition of the raffinate stream can vary from essentially 100% desorbent material to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. At least a portion of the extract stream, and preferably at least a portion of the raffinate stream, from the separation process are passed to separation means, typically fractionators or evaporators, where at least a portion of desorbent material is separated to produce an extract product and a raffinate product. The term "extract product" and "raffinate product" mean products produced by the process containing, respectively an extract component and a raffinate component in higher concentrations than those found in the extract stream and the raffinate stream.

The adsorbents of the present invention have been found to adsorb arabinose selectively over other sugars, more specifically other aldopentoses and aldohexoses. In addition, it has also been found that the initial performance of the adsorbent is maintained during the actual use in the separation process over an economically desirable life. In addition, as previously set forth, the adsorbent of this invention possesses the ability to separate arabinose from other components of the feed, that is, that the adsorbent possesses adsorptive selectivity for one component as compared to other components. The adsorbents used in the separation of this invention are the ion exchange resins in which the exchange sites are exchanged with a mixture of calcium and ammonium ions. The resins may be made by the process described in U.S. Pat. No. 4,444,961, which provides for very uniform spherical size in the polymeric beads. This patent is hereby incorporated in its entirety by reference. As with other adsorbents, the ion exchange resin preferred in the invention has exchange sites exchanged with ammonium ions for part of the calcium ions the resin is initially prepared with. Exchange methods are well known to those of ordinary skill in the art and are suitable for the resins of this invention.

The preferred polymerizable monomers are monomers polymerizable using suspension polymerization techniques. Suspension polymerizable monomers are well known in the art and reference is made to *Polymer Processes*, edited by Calvin E. Schildknecht, published in 1956 by Interscience Publishers, Incorporated, New York, Chapter III, "Polymerization in Suspension" by E. Trommsdoff and C. E. Schildkneckt, pp. 69-109 for purposes of illustration. In Table II on pp. 78-81 of Schildknecht are listed diverse kinds of monomers which can be employed in the practice of this invention. Of such suspension polymerizable monomers, of particular interest herein are the water-insoluble monomers including the monovinylidene aromatics such as styrene, vinylnaphthalene, alkyl substituted styrenes (particularly monoalkyl substituted styrenes such as vinyltoluene and ethyl vinylbenzene) and halo-substituted styrenes such as bromo- or chlorostyrene, the polyvinylidene aromatics such as divinylbenzene, divinyltoluene, divinylxylene, divinylnaphthalene, trivinylbenzene, divinyldiphenyl ether, divinyldiphenyl sulfone and the like; halo olefins particularly the vinyl halides such as vinyl chloride; esters of alpha, beta-ethylenically unsaturated carboxylic acids, particularly acrylic or methacrylic acid, such as methyl methacrylate and ethyl acrylate; vinyl acetate and mixtures of one or more of said monomers. Of said monomers, the monovinylidene aromatics, particularly styrene or a mixture of styrene with a monoalkyl substituted styrene; the polyvinylidene aromatics, particularly divinylbenzene, esters of alpha, beta-ethylenically unsaturated carboxylic acid, particularly methyl methacrylate or combinations thereof, particularly a mixture of styrene and divinylbenzene or styrene, divinylbenzene and methyl methacrylate are preferably employed here.

Also included with the polymerizable monomers useful herein are those monomers which form a solution with a liquid, generally water, wherein the resulting solution is sufficiently insoluble in one or more other liquids, generally a water-immiscible oil or the like, such that the monomer solution forms droplets upon its dispersion in said other liquid. Representative of such monomers are water-soluble monomers which can be polymerized using conventional water-in-oil suspension (i.e., inverse suspension) polymerization techniques such as described by U.S. Pat. No. 2,982,749 which is hereby incorporated by reference, including ethylenically unsaturated carboxyamides such as acrylamide, methacrylamide, fumaramide and ethacrylamide; aminoalkyl esters of unsaturated carboxylic acids and anhydrides; ethylenically unsaturated carboxylic acids, e.g., acrylic or methacrylic acid, and the like. Preferred of such monomers for use herein are the ethylenically unsaturated carboxamides, particularly acrylamide, and the ethylenically unsaturated carboxylic acids, particularly acrylic or methacrylic acid. The monomer phase of such water-soluble monomers will generally contain sufficient amounts of water to solubilize the monomer. In such cases, although the amounts of the monomer and water most advantageously employed will vary depending on many factors including the specific polymer and desired end use application, the monomer generally constitutes less than about 90 weight percent of the monomer phase. Preferably, these water-soluble monomers constitute from about 5 to about 80, more preferably from about 30 to about 55, weight percent of the monomer phase. Normally, the adsorbent will be in the form of particles such as extrudates, aggregates, tablets, macrospheres or granules having a desired particle size range. The adsorbent used in my process will preferably have a particle size range of about 50-100 mesh (Standard U.S. Mesh).

Certain carbohydrates or so-called simple sugars are classified as monosaccharides. These monosaccharides are hydroxyaldehydes or hydroxyketones containing one ketone or aldehyde unit per molecule and two or more alcohol functions. Thus, monosaccharides are classified as aldoses or ketoses on the basis of their carbonyl unit. Ketoses and aldoses are further classified by their carbon skeleton length. Accordingly, 5 carbon and 6 carbon monosaccharides receive the respective names of pentoses and hexoses. Well-known aldohexoses include glucose, mannose and galactose. Arabinose and xylose are well-known aldopentoses. This invention is a process for separating arabinose from other aldopentoses and aldohexoses.

Consequently, feed mixtures which can be utilized in the process of this invention will comprise a mixture of arabinose and at least one other aldose. Potential feed mixtures containing substantial quantities of aldoses to the substantial exclusion of other monosaccharides are typically found in plant tissue hydrolysates, wood or beet pulp. Such mixtures will usually contain significant quantities of such monosaccharides as xylose, arabinose, mannose, glucose, and galactose. Apart from these more common sugars, feed mixtures derived from natural sources will also contain quantities of lesser known monosaccharides. A typical feed mixture for this invention will contain 20-30% xylose, 15-20% arabinose, 0.5-3% mannose, 40-60% glucose, and 1-5% galactose based on weight percent of solids. In addition, there may be up to 10 wt. % solids of other lesser known sugars. However, this invention is not limited to the separation of naturally derived feed mixtures but also includes separating arabinose from other aldoses in sugar mixtures that are synthetically prepared or produced by the processing of carbohydrates.

Although it is not clear what properties of the adsorbent are responsible for the arabinose separation herein described, it appears that it cannot be attributed to pore size selectivity alone. Since arabinose is separated from sugar molecules of similar size, it appears that steric factors as well as electrostatic attraction action play an important role in the separation. While it is not possible to conclusively set forth the molecular interaction responsible for the adsorption, one possible explanation is a combination of cation attraction which varies the orientation of specific sugar molecules to the pore opening on the adsorbent. This varied orientation can provide a suitable disposition of the particular structural configuration corresponding to certain sugar molecules which coincides with the shape of the adsorbent pore openings as altered by the presence of specific cations. Therefore, both electrostatic interaction as well as physical and stoichiochemical considerations may provide the mechanism for this separation.

Although it is possible by the process of this invention to produce high purity arabinose, it will be appreciated that an extract component is never completely adsorbed by the adsorbent, nor is a raffinate component completely unadsorbed by the adsorbent. Therefore, small amounts of a raffinate component can appear in the extract stream, and likewise, small amounts of an extract component can appear in the raffinate stream. The extract and raffinate streams then are further distinguished from each other and from the feed mixture by the ratio of the concentrations of an extract component and a specific raffinate component, both appearing in the particular stream. For example, the ratio of concentration of the more selectively adsorbed arabinose to the concentration of less selectively adsorbed sugars will be highest in the extract stream, next highest in the feed mixture, and lowest in the raffinate stream. Likewise, the ratio of the less selectively adsorbed sugars to the more selectively adsorbed arabinose will be highest in the raffinate stream, next highest in the feed mixture, and the lowest in the extract stream.

Desorbent materials used in various prior art adsorptive separation processes vary depending upon such factors as the type of operation employed. In the swing bed system, in which the selectively adsorbed feed component is removed from the adsorbent by a purge stream, desorbent selection is not as critical. However, in adsorptive separation processes which are generally operated continuously at substantially constant pressures and temperatures to ensure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity (hereinafter discussed in more detail), it is preferred that the adsorbent be more selective for all of the extract components with respect to a raffinate component than it is for the desorbent material with respect to a raffinate component. Secondly, desorbent material must be compatible with the particular adsorbent and the particular feed mixture. More specifically, they must not reduce or destroy the critical selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent in admixture with desorbent material and any chemical reaction involving a desorbent material and an extract component or a raffinate component would reduce the purity of the extract product or the raffinate product or both. Since both the raffinate stream and the extract stream typically contain desorbent material, desorbent materials should additionally be substances which are easily separable from the feed mixture that is passed into the process. Without a method of separating at least a portion of the desorbent material present in the extract stream and the raffinate stream, the concentration of an extract component in the extract product and the concentration of a raffinate component in the raffinate product would not be very high, nor would the desorbent material be available for reuse in the process. It is contemplated that at least a portion of the desorbent material will be separated from the extract and the raffinate streams by distillation or evaporation, but other separation methods such as reverse osmosis may also be employed alone or in combination with distillation or evaporation. Since the raffinate and extract products are foodstuffs intended for human consumption, desorbent material should also be nontoxic. Finally, desorbent materials should also be materials which are readily available and therefore reasonable in cost. A suitable and preferred desorbent for this separation is water.

The prior art has recognized that certain characteristics of adsorbents and desorbents are highly desirable, if not absolutely necessary, to the successful operation of a selective adsorption process. Such characteristics are equally important to this process. Among such characteristics are: adsorptive capacity for some volume of an extract component per volume of adsorbent; the selective adsorption of an extract component with respect to a raffinate component and the desorbent material; and sufficiently fast rates of adsorption and desorption of an extract component to and from the adsorbent. Capacity of the adsorbent for adsorbing a specific volume of an extract component is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate an extract component of known concentration contained in a particular charge rate of feed mixture. A reduction in the amount of adsorbent required for a specific adsorptive separation reduces the cost of a separation process. It is important that the good initial capacity of the adsorbent be maintained during actual use in the separation process over some economically desirable life. The second necessary adsorbent characteristic is the ability of the adsorbent to separate components of the feed; or, in other words, that the adsorbent possess adsorptive selectivity, (B), for one component as compared to another component.

Relative selectivity can be expressed not only for one feed component as compared to another but can also be expressed between any feed mixture component and the desorbent material. The selectivity, (B), is defined as the ratio of the two components of the adsorbed phase over the ratio of the same two components in the unadsorbed phase at equilibrium conditions. Relative selectivity is shown as Equation 1, below:

$$\text{Selectivity} = (B) \frac{[\text{wt. percent } C/\text{wt. percent } D]_A}{[\text{wt. percent } C/\text{wt. percent } D]_U} \quad \text{Equation 1}$$

where C and D are two components of the feed represented in weight percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases. Where selectivity of two components approaches 1.0, there is no preferential adsorption of one component by the adsorbent with respect to the other; they are both adsorbed (or nonadsorbed) to about the same degree with respect to each other. As the (B) becomes less than or greater than 1.0, there is a preferential adsorption by the adsorbent for one component with respect to the other. When comparing the selectivity by the adsorbent of one component C over component D, a (B) larger than 1.0 indicated preferential adsorption of component C within the adsorbent. A (B) less than 1.0 would indicate that component D is preferentially adsorbed leaving an unadsorbed phase richer in component C and an adsorbed phase richer in component D. Ideally, desorbent materials should have a selectivity equal to about 1 or lightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is just slightly greater than 1.0, it is preferred that such selectivity be reasonably greater than 1.0. Like relative volatility, the higher the selectivity the easier the separation is to perform. Higher selectivities permit a smaller amount of adsorbent to be used. The third important characteristic is the rate of exchange of the extract component of the feed mixture material, or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

Resolution is a measure of the degree of separation of a two-component system, and can assist in quantifying the effectiveness of a particular combination of adsorbent, desorbent, conditions, etc. for a particular separation. Resolution for purposes of this application is defined as the distance between the two peak centers divided by the average width of the peaks at ½ the peak height as determined by the pulse tests described hereinafter. The equation for calculating resolution is thus:

$$R = \frac{L_2 - L_1}{\frac{1}{2}(W_1 + W_2)}$$

where $L_1$ and $L_2$ are the distance, in ml, respectively, from a reference point, e.g., zero to the centers of the peaks and $W_1$ and $W_2$ are the widths of the peaks at ½ the height of the peaks.

The adsorption-desorption operations may be carried out in a dense fixed bed which is alternatively contacted with a feed mixture and a desorbent material in which case the process will be only semicontinuous. In another embodiment, generally referred to as a swing bed system, a set of two or more static beds of adsorbent may be employed with appropriate valving so that a feed mixture can be passed through one or more adsorbent beds of a set while a desorbent material can be passed through one or more of the other beds in a set. The flow of a feed mixture and a desorbent material may be either up or down through an adsorbent in such beds. Any of the conventional apparatus employed in static bed fluid-solid contacting may be used.

Moving bed or simulated moving bed flow systems, however, have a such greater separation efficiency than fixed bed systems and are therefore preferred. In the moving bed or simulated moving bed processes, the retention and displacement operations are continuously taking place which allows both continuous production of an extract and a raffinate stream and the continual use of feed and displacement fluid streams. One preferred embodiment of this process utilizes what is known in the art as the simulated moving bed countercurrent flow system. In such a system, it is the progressive movement of multiple liquid access points down a molecular sieve chamber that simulates the upward movement of molecular sieve contained in the chamber. Reference can also be made to D. B. Broughton's U.S. Pat. No. 2,985,589, in which the operating principles and sequence of such a flow system are described, and to a paper entitled, "Continuous Adsorptive Processing—A New Separation Technique" by D. B. Broughton presented at the 34th Annual Meeting of the Society of Chemical Engineers at Tokyo, Japan on Apr. 2, 1969, both references incorporated herein by reference, for further explanation of the simulated moving bed countercurrent process flow scheme.

Another embodiment of a simulated moving bed flow system suitable for use in the process of the present invention is the cocurrent high efficiency simulated moving bed process disclosed in U.S. Pat. No. 4,402,832 to Gerhold, incorporated by reference herein in its entirety.

While this invention may be practiced in any type of flow system, the manner of operation will affect desorbent selection. Swing bed systems are less sensitive to desorbent selection so that the process is likely to perform well with any material from the aforementioned broad class of desorbents. However, in adsorptive separation processes which are generally operated continuously at substantially constant pressures and temperatures to ensure liquid phase, the desorbent material relied upon must be selected more judiciously. It is in the continuous separation processes where the previously described class of preferred desorbents will offer the greatest advantages.

It is contemplated that at least a portion of the extract output stream will pass into a separation means wherein at least a portion of the desorbent material can be separated at separating conditions to produce an extract product containing a reduced concentration of desorbent material. Preferably, but not necessary to the operation of the process at least a portion of the raffinate output stream will also be passed to a separation means wherein at least a portion of the desorbent material can be separated at separating conditions to produce a desorbent stream which can be reused in the process and a raffinate product containing a reduced concentration of desorbent material. Typically, the concentration of desorbent material in the extract product and the raffinate product will be less than about 5 vol. % and more preferably less than about 1 vol. %. The separation means will typically be a fractionation column, the design and operation of which is well known to the separation art.

Although both liquid and vapor phase operations can be used in many adsorptive separation processes, liquid-phase operation is required for this process because of the lower temperature requirements and because of the higher yields of extract product that can be obtained with liquid-phase operation over those obtained with vapor phase operation. Adsorption conditions will include a temperature range of from about 20° C. to about 200° C. with about 20° C. to about 100° C. being preferred and a pressure range of from about atmospheric to about 500 psig with from about atmospheric to whatever pressure is required to ensure liquid phase being preferred. Desorption conditions will include the same range of temperatures and pressures as used for adsorption conditions.

The size of the units which can utilize the process of this invention can vary anywhere from those of pilot plant scale (see for example our assignee's U.S. Pat. No. 3,706,812) to those of commercial scale and can range in flow rates from as little as a few cc an hour up to many thousands of gallons per hour.

A dynamic testing apparatus may be employed to test various adsorbents with a particular feed mixture and desorbent material to measure the adsorbent characteristics of adsorptive capacity, selectivity and exchange rate. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to detect qualitatively or determine quantitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of feed containing known concentrations of a nonadsorbed polysaccharide tracer, Maltrin-DP4+ aldoses, and other trace sugars, all diluted in desorbent, is injected for a duration of several minutes. Desorbent flow is resumed, and the tracer and the aldoses are eluted as in a liquid-solid chromatographic operation. The effluent is collected in fractions and analyzed using chromatographic equipment and traces of the envelopes of corresponding component peaks developed.

From information derived from the test, adsorbent performance can be rated in terms of retention volume for an extract or a raffinate component, selectivity for one component with respect to the other, and the rate of desorption of an extract component by the desorbent. The retention volume of an extract or a raffinate component may be characterized by the distance between the center of the peak envelope of an extract or a raffinate component and the peak envelope of the tracer component or some other known reference point. It is expressed in terms of the volume in cubic centimeters of desorbent pumped during this time interval represented by the distance between the peak envelopes. Selectivity, (B), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width the faster the desorption rate.

The following example shown below is intended to further illustrate the process of this invention and is not to be construed as unduly limiting the scope and spirit of said process. The example presents test results for the adsorbent and desorbent materials of the invention when using the above dynamic testing apparatus.

EXAMPLE I

In this example, a test was run using a nuclearly-substituted sulfonated cation exchange resin having a cross-linked divinylbenzene resin matrix (Dowex 99) having 2.6% Ca ions and 5.5% nitrogen as ammonium ions at cation exchange sites to determine the separation of arabinose from a carbohydrate mixture. The adsorbent was packed in a 8.4 mm diameter column having a total volume of 70 cc. The feed mixture consisted of 30 gm of the carbohydrate mixture given in Table 1 diluted with 70 ml of distilled water resulting in a solution containing 30% of solids.

TABLE 1

| | Wt. % Dry Solids |
|---|---|
| Xylose | 5 |
| Glucose | 5 |
| Arabinose | 5 |
| Mannose | 5 |
| Galactose | 5 |
| Maltrin (tracer) | 5 |
| Water | 70 |
| | 100 |

The experiment began by passing a water desorbent through the column at a flow rate of 1.2 cc/min. and a temperature of 65° C. At a convenient time, 10 ml of feed was injected into the column after which flow of desorbent was immediately resumed. FIG. 1 provides a graphical representation of the adsorbent's relative retention of the sugars and hence the ability to separate arabinose from the other monosaccharides.

A consideration of the average midpoint for each concentration curve reveals a good separation of arabinose from the other feed mixture sugars. Arabinose is clearly the most selectively retained component. From the data obtained from this experiment the net retention volume, selectivities and resolution of Table 2 were calculated.

TABLE 2

| | B | Net Retention Volume | Peak Width at ½ Height | Resolution |
|---|---|---|---|---|
| Arabinose/Mannose | 1.19 | 17.9 | 12.5 | .26 |
| Arabinose/Glucose | 1.53 | 13.9 | 11.9 | .59 |
| Arabinose/Xylose | 1.26 | 16.8 | 11.9 | .36 |
| Arabinose/Galactose | 1.23 | 17.3 | 12.2 | .31 |

Both selectivities and resolutions clearly establish the achievement of a high degree of separation for arabinose form mannose, glucose, xylose and galactose.

EXAMPLE II

This example was carried out similar to the one described in Example I. The only difference was the test was run using Dowex 99 resin having 8.7% Ca to determine the separation of arabinose from a carbohydrate mixture. The data obtained from this study—net retention volume, selectivity and resolution were calculated and reported in Table 3.

TABLE 3

| | B | Net Retention Volume | Peak Width at ½ Height | Resolution |
|---|---|---|---|---|
| Arabinose/Mannose | 1.16 | 18.1 | 14 | 0.20 |
| Arabinose/Glucose | 1.48 | 14.2 | 10.9 | 0.52 |
| Arabinose/Xylose | 1.23 | 17.1 | 12.6 | 0.28 |
| Arabinose/Galactose | 1.20 | 17.5 | 13.2 | 0.25 |

Figure 2:
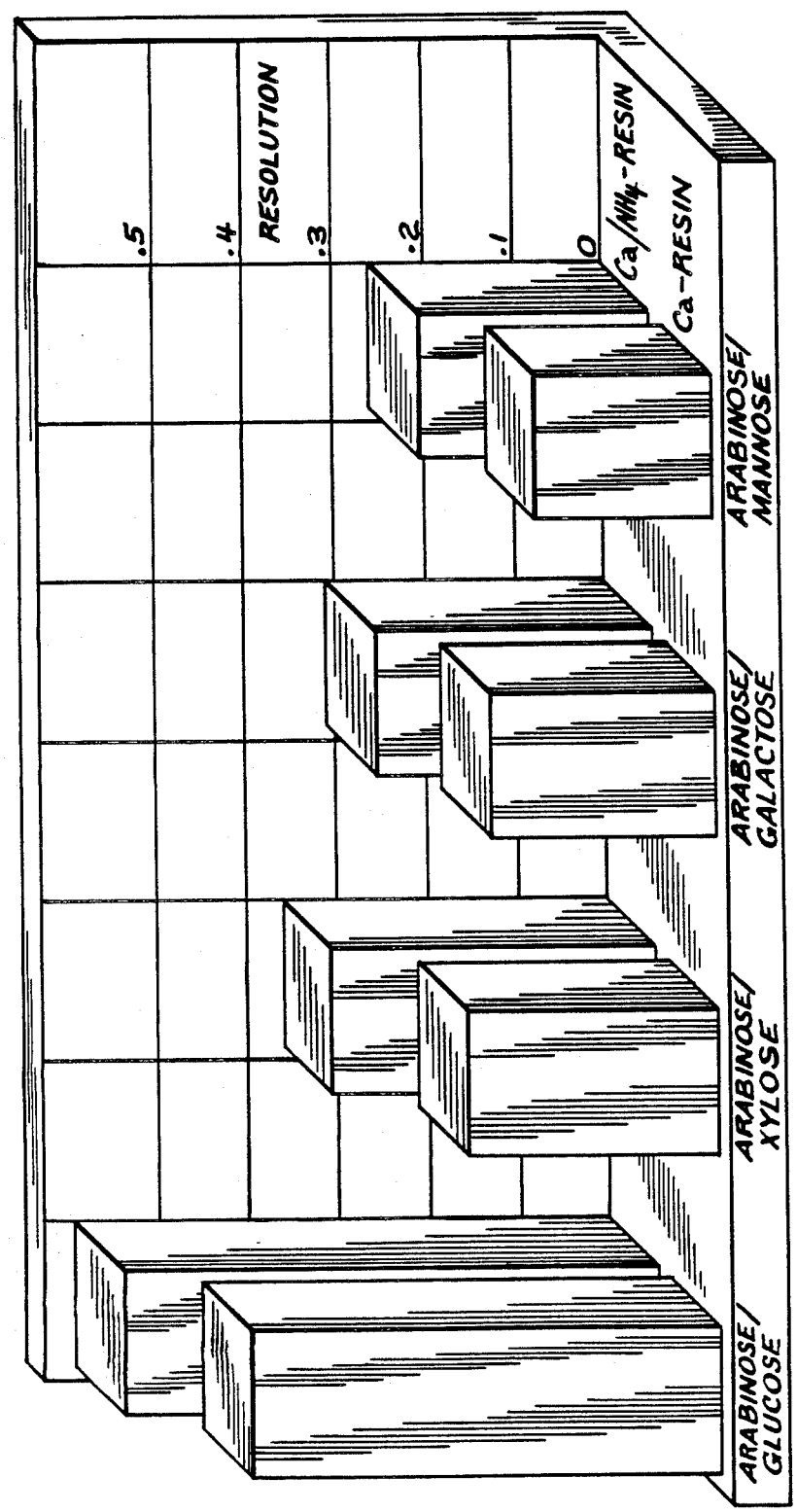

Both selectivities and resolutions indicated that some degree of separation of arabinose from mannose, glucose, xylose and galactose was possible. However, Tables 2 and 3 indicate that the Ca/NH$_4$-resin is a far better performer in the arabinose separation than the Ca-resin. The difference can be noted clearly from the lower resolution achieved with the Ca-resin (Table 3) than that achieved by the Ca/NH$_4$-resin (Table 2). This difference is also demonstrated in FIG. 2, in which resolution is plotted for Ca-resin and Ca/NH$_4$-resin. There is higher resolution in all cases for Ca/NH$_4$-resin compared to Ca-resin.

What is claimed is:

1. A process for separating arabinose rom an aqueous feed mixture containing arabinose and at least one other monosaccharide, selected from the group consisting of aldopentoses and aldohexoses, which comprises contacting at adsorption conditions said mixture with an adsorbent comprising a nuclearly sulfonated cationic exchange resin having a crosslinked vinylaromatic resin matrix exchanged with Ca$^{++}$ and NH$_4^+$ ions, selectively adsorbing said arabinose to the substantial exclusion of the other monosaccharides, removing the nonadsorbed portion of the feed mixture from contact with the adsorbent, and hereafter recovering high purity arabinose by desorption at desorption conditions.

2. The process of claim 1 wherein said feed mixture contains arabinose and at least one other monosaccharide selected form the group consisting of xylose, glucose, galactose, mannose, and rhamnose.

3. The process of claim 1 wherein said desorbent comprises water.

4. The process of claim 3 wherein said exchange resin is a sulfonated polystyrene polymer having a crosslinked divinylbenzene matrix.

5. The process of claim 4 wherein said exchange resin is crosslinked from about 4% to 6%.

6. The process of claim 5 wherein said separation is effected by a countercurrent simulated moving bed scheme.

7. The process of claim 5 wherein said separation is effected by a cocurrent simulated moving bed scheme.

* * * * *